US005762889A

United States Patent [19]
Hopper

[11] Patent Number: 5,762,889
[45] Date of Patent: Jun. 9, 1998

[54] AUTOCLAVE WITH HEAT CHAMBER HAVING SLIDING PERIPHERAL WALL

[76] Inventor: James A. Hopper, 2474 Matterhorn Dr., Wexford, Pa. 15090

[21] Appl. No.: 813,580

[22] Filed: Mar. 7, 1997

[51] Int. Cl.⁶ .................................................. A61L 2/00
[52] U.S. Cl. ...................... 422/295; 422/292; 422/297; 422/300; 422/307
[58] Field of Search .................................. 422/295, 297, 422/300, 26, 307, 292

[56] References Cited

U.S. PATENT DOCUMENTS

| | | |
|---|---|---|
| 3,488,142 | 1/1970 | Cooper .................. 422/295 X |
| 3,511,593 | 5/1970 | Thomas et al. ............ 422/295 |
| 4,082,510 | 4/1978 | Jovanovic . | 
| 4,098,490 | 7/1978 | Morrison . |
| 5,002,196 | 3/1991 | Bassili . |
| 5,470,547 | 11/1995 | Lhenry .................... 422/295 |
| 5,622,678 | 4/1997 | Hiltawsky et al. ........ 422/295 |

Primary Examiner—Krisanne Thornton
Attorney, Agent, or Firm—Terrance L. Siemens

[57] ABSTRACT

An autoclave having end walls sturdily attached to one another by rods and a mobile, cylindrical lateral wall. When the lateral wall is moved into an operable position over the end walls, thereby sealing a working chamber defined between the end walls and when steam is introduced into the working chamber, each end wall will counteract pressure acting on its opposing counterpart. The autoclave need not be reinforced to hold the walls together. The rods connecting the end walls are hollow, and have ports disposed within the working chamber, so that steam may be introduced into the working chamber through these rods. Air from within the working chamber may also be vented by the rods. The lateral wall is vertically oriented and moved. A retaining wall traps condensate, which would otherwise escape when the lateral wall is lifted. An optional powered apparatus lifts and lowers the lateral wall into positions respectively exposing and sealing the working chamber. In a further option, the lateral wall is frustoconical rather than cylindrical, thereby avoiding sliding contact with the end walls.

12 Claims, 3 Drawing Sheets

AUTOCLAVE WITH HEAT CHAMBER HAVING SLIDING PERIPHERAL WALL

BACKGROUND OF THE INVENTION

1. Field of the Invention

The present invention relates to pressure vessels, and more particularly to a pressure vessel having a slidably removable, cylindrical lateral wall and fixed end walls. The end walls are mutually connected by rods passing through the interior of the closed vessel. The rods both reinforce the endwalls against blowout and also conduct fluids such as steam for treating objects placed inside the pressure vessel.

2. Description of the Prior Art

Pressure vessels operating at pressures greater than surrounding ambient pressure are subject to bursting, and must be designed to resist bursting. It is customary to exploit certain properties of geometric solids to minimize stoutness of construction when providing requisite strength. For example, containers of compressed gas are frequently cylindrical along their length, with domed ends. This configuration is easily fabricated, and presents few problems when storing compressed gasses.

However, for ovens such as autoclaves, which must be loaded with objects which are treated with steam and subsequently removed, it is not feasible to employ construction appropriate for gas storage. A door must be provided for inserting and retrieving treated objects. The door is frequently located at one end of a cylindrical body, so that a lateral wall may comprise an uninterrupted cylinder. The end wall must be reinforced against both buckling and against expulsion from the cylinder.

An example of this situation is shown in U.S. Pat. No. 5,002,196, issued to John Bassili on Mar. 26, 1991. A retaining member is placed over an end of the pressure vessel, and is secured to the exterior of the cylindrical body. The retaining member must be carefully and securely fixed to the cylindrical body. By contrast, the present invention includes rods disposed inside the pressure vessel which span both ends, and firmly connect one to the other. This construction assures that each end will counteract pressure operating on the other end. Therefore, no complicating apparatus must be provided for securing each end to the cylindrical body.

A pressure vessel utilizing mutually connected end walls is shown in U.S. Pat. No. 4,082,510, issued to Dragomir Jovanovic on Apr. 4, 1978. However, Jovanovic reverses the concept of the present invention. Jovanovic fixes the cylindrical lateral wall to the base of the pressure vessel and slides the ends longitudinally between open and closed positions.

By contrast, in the present invention, the ends are fixed to the base and the cylindrical body is moved relative to the base. This affords a significant advantage over Jovanovic. That is, rods connecting the ends are fixed to the base and may be exploited to conduct fluids into and out of the chamber. Therefore, the novel construction enables steam to be delivered into the chamber when sealed, and atmospheric gasses to be evacuated from the sealed chamber when desired. These functions cannot be performed by the device of Jovanovic without penetrating the cylindrical body. Also, in the present invention, the cylindrical body is fully removable from the pressure vessel. By contrast, in the device of Jovanovic, the cylindrical body and end wall assembly are captively joined to one another. Even further, it becomes practical to mount controls and other ancillary devices in one or both end walls of the novel pressure vessel.

Neither one of the above inventions and patents, taken either singly or in combination, is seen to describe the instant invention as claimed.

SUMMARY OF THE INVENTION

The present invention improves upon known autoclaves by introducing new features and benefits. The novel autoclave includes a cylindrical lateral wall which slides into engagement with an assembly comprising two end walls fixed to one another by a plurality of connecting rods spanning the end walls. When the lateral wall is in place, a chamber is defined between the end walls and inside the lateral wall. This chamber is the working chamber which contains items being subject to processing.

The novel autoclave enjoys the advantages of a cylindrical pressure vessel having end walls fixed to one another. Each end wall reinforces its opposed counterpart, so that the function of reinforcement of any end wall need not fall upon the lateral wall nor on any other member of the autoclave. In the novel arrangement, a plurality of rods passing through the working chamber connects the end walls. This arrangement provides sufficient support to each end wall such that the end walls need not be domed.

For its part, the lateral wall spanning the end walls and thereby completing enclosure of the working chamber exploits cylindrical configuration, so that massive or reinforced construction need not be provided. Pressure forces acting radially outwardly upon the cylindrical lateral wall are counteracted in part by circular configuration of this wall, thereby minimizing thickness or strength of the constituent material of this wall.

Thus, the combination of mutually reinforcing end walls and a lateral wall having circular configuration both increases strength of the pressure vessel, and also minimizes pressure required to be exerted on either end wall and on the lateral wall to assure effective sealing of the pressure vessel.

The connecting rods pass through the working chamber, so that the end walls comprise a unitary or fixed assembly. The end wall assembly is fixed to a base of the autoclave with the longitudinal axis of the working chamber vertically oriented. Therefore, the lateral wall is pulled upwardly to expose items being treated. This configuration is useful since steam treatment of objects normally generates condensate. A peripheral wall for retaining condensate is attached to the lower end plate. Therefore, when the lateral wall is drawn upwardly, thus exposing the working chamber, condensate is trapped and does not spill onto environmental surfaces and other objects.

The lateral wall is fully removable from engagement with the end wall assembly. This feature expedites replacement of the end wall assembly, if required, and improves access to the working chamber. Full access to the working chamber enables the entire volume thereof to be utilized.

The connecting rods spanning and retaining the end walls are hollow, and communicate with the working chamber through ports. Steam may be introduced into the working chamber and displaced air removed through the connecting rods. Neither the lateral wall nor end walls need be interrupted to provide steam entry and air evacuation ports. A liquid circuit having appropriate valves and filters enables the working chamber to be charged and vented.

Optionally, the autoclave includes a powered element for moving the lateral wall between an operable position, wherein the lateral wall is lowered over the end walls, thereby sealing the working chamber, and a retracted position exposing and affording access to the working chamber.

In a further option, the lateral wall of the chamber is frustoconical rather than cylindrical. This configuration does not contravene structural advantages of a cylindrical lateral wall, since at each cross section taken perpendicularly with respect to its length, the lateral wall remains circular. In this embodiment, sealing is enhanced since downward pressure against the lateral wall compresses O-rings or corresponding gaskets or seals for sealing the chamber. This embodiment further expedites removal of the lateral wall should a seal distort, thereby causing the lateral wall to bind.

Accordingly, it is an object of the invention to provide an autoclave which has a working chamber wherein opposed walls are mutually connected, so that internal pressure pressing outwardly on each wall is counteracted by an opposed wall.

It is another object of the invention to provide an autoclave wherein end walls are fixed and a lateral wall is removable from the end walls.

It is a further object of the invention to orient the mobile or removable wall of the working chamber vertically.

Still another object of the invention is to provide structure for retaining condensate within the autoclave when the lateral wall is moved to the retracted position.

An additional object of the invention is to utilize structural members connecting opposed end walls as fluid conduits for injecting steam into and evacuating the working chamber.

It is again an object of the invention to provide powered apparatus for moving the lateral wall to the retracted position and to the operable position.

Yet another object of the invention is to provide a frustoconical lateral wall for the working chamber.

Still another object of the invention is to fully disengage the lateral wall from both end walls.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
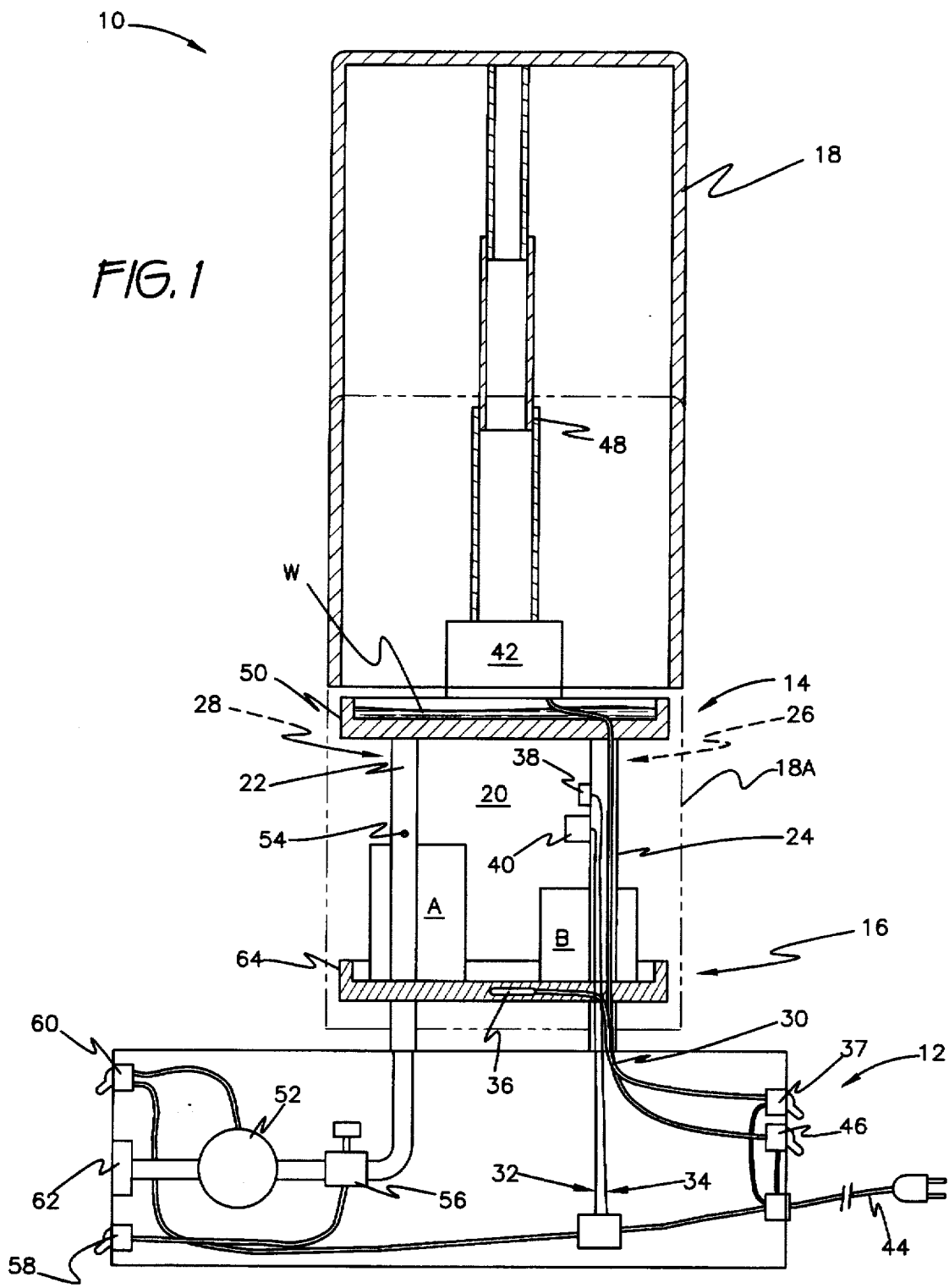
FIG. 1 is an environmental, side elevational, partially cross sectional view of the invention, partially broken away to reveal internal detail.

Turning now to FIG. 1, novel autoclave 10 is seen to comprise fixed or stationary components including a base 12 and upper and lower end walls 14, 16 (respectively), and a mobile component comprising the outer or lateral wall 18. Lateral wall 18 is preferably cylindrical, and is moved between a retracted position and an operable position. Retraction can be upward or downward, FIG. 1 shows an upward retraction. A working chamber, generally designated at 20, is defined between upper and lower end walls 14, 16 when lateral wall 18 is lowered into the operable position, as indicated in broken lines at 18A. In the operable position, lateral wall 18 spans end walls 14 and 16, thereby enclosing and sealing working chamber 20. Working chamber 20 will be understood to comprise solid members enclosing a working space therein.

Base 12 provides a stable structure for supporting autoclave 10 on an environmental surface in the general vertical orientation shown in FIG. 1. Vertical orientation signifies that the working space within working chamber 20 is revealed and enclosed by vertical travel of lateral wall 18, and that upper and lower ends walls 14, 16 are mounted above base 12.

Upper and lower end walls 14, 16 are opposed, in that they are located on opposite sides of working chamber 20, and are connected by connecting rods 22, 24, 26, 28. Rods 22, 24, 26, 28 are mounted in base 12 and extending upwardly through lower end wall 16 to both connect opposing walls 14, 16 so solidly that walls 14, 16 need not be either domed or unduly thick, and also to serve as conduits. Rods 22, 24, 26, 28 have passages formed therein and extending longitudinally entirely through rods 22, 24, 26, 28. These passages conduct fluids in a manner to be described hereinafter, and also to enclose electrical conductors 30, 32, and 34 which conduct power to an electrical heating element 36 and to pressure sensors 38, 40. Location of heating element 36 within lower end wall 16 provides heat for generating steam within chamber 20 or conserves heat which may be lost should a steam generating chamber (not shown) be located remotely from working chamber 20. Openings formed in connecting rods 22, 24, 26, 28 are provided where appropriate to enable electrical conductors and fluid to pass as described. Other electrical conductors (not shown) could also be provided for temperature sensors and humidity sensing.

Electrical power is utilized to perform various functions, and is provided by connecting a conventional power cord 44 into an electrical receptacle (not shown). Power conductors branch so as to serve separately switched functions. Heating element 36 is controlled by a switch 37.

42 represents any suitable powered actuator for moving lateral wall 18 into the operable and retracted positions. Actuator 42 has a telescoping arm 48 supporting lateral wall 18. Actuator 42 may comprise an electric gear motor and a suitable linkage (not shown). Actuator 42 is operated by switch 46. Alternatively, actuator 42 may be driven by spring, vacuum, or positive fluid pressure, or in any other suitable way if electrical power is not utilized.

Actuator 42 preferably fully disengages lateral wall 18 from end walls 14, 16, as shown, thereby affording maximum access to items being treated. Illustratively, two representative items A, B are shown placed on lower end wall 16, which also serves as a tray or similar horizontal supporting surface for accommodating items being treated in autoclave 10.

Water W for treating items is contained within a reservoir formed in upper end wall 14 by a low wall or lip 50 projecting upwardly from end wall 14. Water is drawn by vacuum into working chamber 20 in a manner to be described hereinafter.

Air occupying working chamber 20 is evacuated when lateral wall 18 is in the operable position by vacuum pump 52. Air flows through at least one connecting rod 22, 24, 26, or 28, communicating between a passage formed in rod 22, 24, 26, or 28 and the working space within working chamber 20 through an opening 54. A valve 56 controls communication between chamber 20 and vacuum pump 52, valve 56 is actuated by switch 58.

Power serving vacuum pump 52 is controlled by a switch 60, and is overridden by pressure sensor 38. Pressure sensor 38 is a low pressure switch, and is arranged to assure that power to vacuum pump 52 is discontinued when switch 60 is in the "on" position and when the pressure within working chamber 20 drops below a predetermined limit. This arrangement assures that proper working conditions are achieved when subjecting items A, B to steam treatment. It also assures the proper pressure differential when water is injected to make steam. Air escaping from vacuum pump 52 is filtered by a filter 62 prior to release to the atmosphere, to retain objectionable or hazardous substances. The vacuum pump 52 is also used for drying processed items following steam processing by creating sub atmospheric conditions. Pressure switch 40 is an on/off switch that connects to heater 36 in an alternative operation. The pressure switch 40 is set at a pressure that corresponds to the steam saturation temperature. Thereby when controlling pressure at known saturation conditions the temperature is also controlled A low wall 64 projecting upwardly at the periphery of lower end wall 16 serves as a condensate retainer, for constraining condensate generated by operation of autoclave 10 against escaping when lateral wall 18 is moved to the retracted position after operation of autoclave 10. Wall 64 could be located on the upper surface of base 12, if desired. This alternative location would be appropriate if lower end wall 16 were in close proximity to or abutting base 12. A containment wall is also achieved when the lateral wall is inverted and pulled partially downward (not shown).

Figure 2:
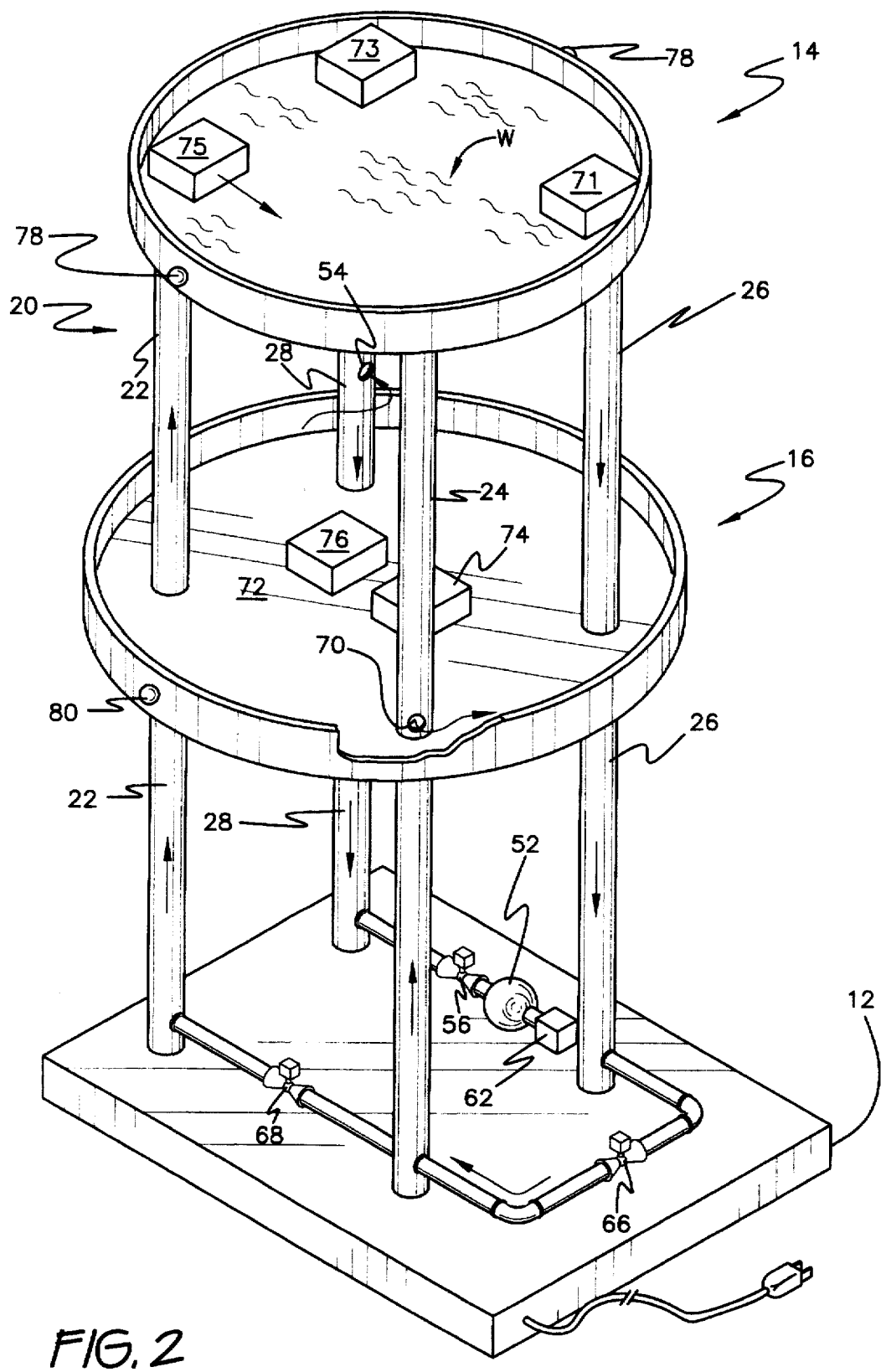
FIG. 2 is a perspective, diagrammatic detail view of the stationary components of the invention.

A preferred fluid flow and control scheme is shown in FIG. 2. The reservoir formed above upper end wall 14 is partially charged with water W. With valve 56 in the open position, vacuum pump 52 is operated. Air occupying working chamber 20 is evacuated through opening 54 and flows through connecting rod 28 to vacuum pump 52, ultimately escaping to the atmosphere after passing through filter 62. Vacuum in working chamber 20 causes water W stored in the reservoir to be drawn through connecting rod 26 when a valve 66 is open and a valve 68 is closed. Water is drawn into working chamber 20 through an opening 70 formed in connecting tube 24. Opening 70 is preferably located such that the bottom of opening 70 is even with the upper surface 72 of lower end wall 16. Valves 56, 66 and 68 are shown but other types of valve such as solenoid valves or any other valves known in the art could be used.

Water passes through a filter 71 prior to entering rod 26. The passage within rod 28 extends to the upper surface of upper end wall 14, and passes through a one way relief valve 73. Should excessive pressure develop within working chamber 20, steam will escape upwardly through pressure relief valve 73. Steam is baffled to the exterior ambient room conditions. A diffuser 75 is disposed at the upper end of the passage formed in connecting rod 22. After processing is complete solenoid valve 68 is opened and the pressurized fluid contents of chamber 10 are discharged into the reservoir. Condensate from the steam is returned to water W within the reservoir When vacuum has drawn a desired amount of water into working chamber 20, which may be signaled by a level sensor 74, heating element 36 (see FIG. 1) is energized by operating switch 37 or by pressure switch 40 or by direct temperature sensing. An over temperature sensor 76 overrides switch 37 or other control to discontinue power to heating element 36 if a predetermined temperature or condition is exceeded. Although electrical conductors serving sensors 74 and 76 are not shown, they will be provided where required to achieve functions set forth herein, and will be contained within a connecting rod 22, 24, 26, or 28. Any one or several of rods 22, 24, 26, 28 may have two separate passages, one devoted to fluids and the other devoted to electrical conductors. Dimensions of any rod 22, 24, 26, or 28 may be adjusted to accommodate the several tasks demanded thereof.

Sealing of chamber 20 is accomplished by seals 78, 80, which is depicted as comprising O-rings. Of course, seals 78, 80 are merely representative of any type and location of seal which may be utilized. Any suitable resilient or non-resilient passive or active seals may be substituted for the O-rings shown. Seals 78, 80 make sealing contact with lateral wall 18 when the latter is in the operable position.

Figure 3:
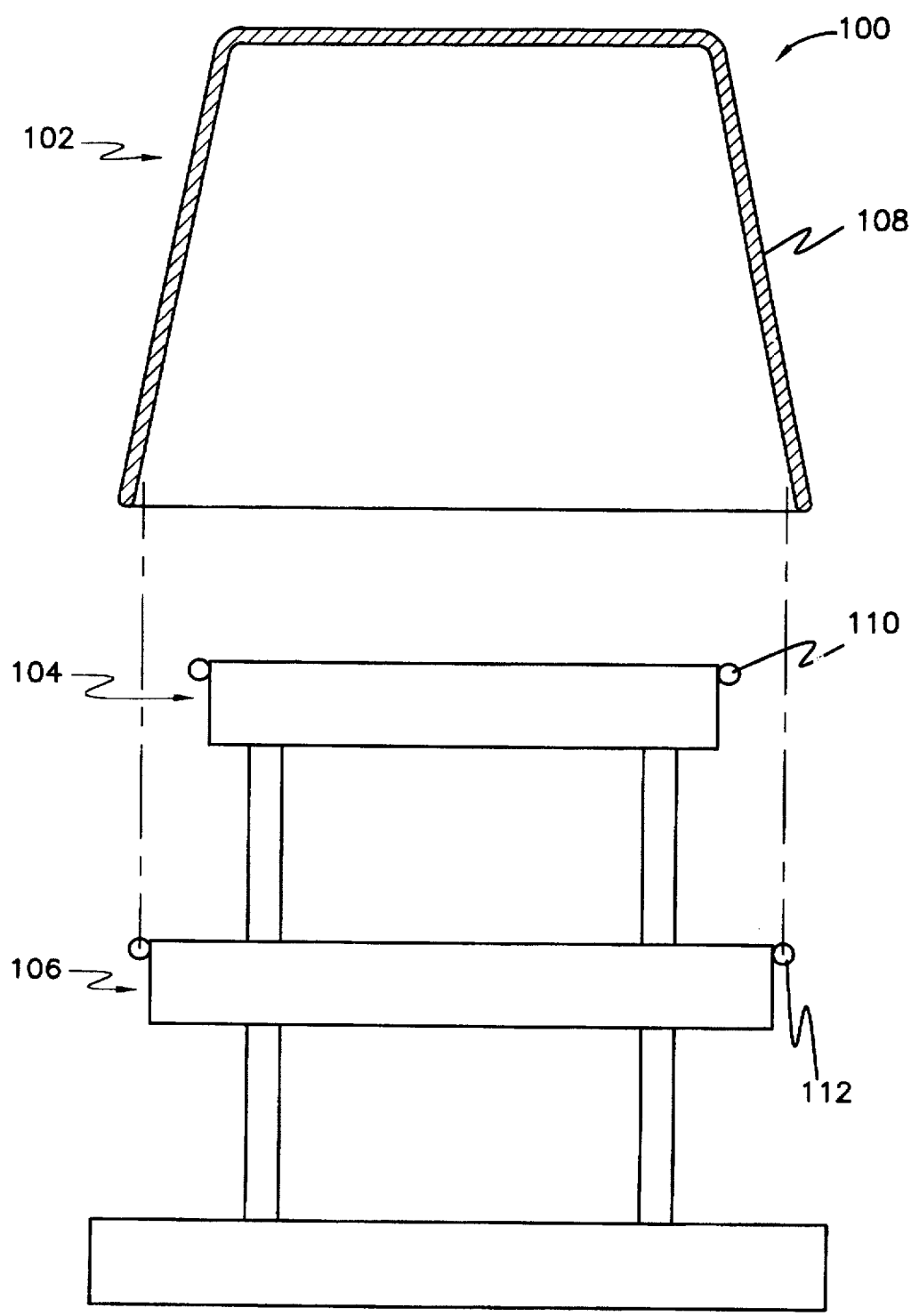
FIG. 3 is a side elevational, partially cross sectional view of an alternative embodiment of the invention.

A modification to the embodiments of FIGS. 1 and 2 is shown in FIG. 3, wherein autoclave 100 has a frustoconical lateral wall 102 oriented such that its relatively large end is located below its relatively small end. This arrangement avoids sliding contact when lateral wall 102 makes sealing contact with upper end wall 104 and lower end wall 106.

Upper end wall 104 is of reduced diameter, compared to that of lower end wall 106. The relative diameters cooperate with inclination of the lateral panel 108 of lateral wall 102, so that when lateral wall 102 is lowered into an operable position corresponding to that of FIG. 2, contact of panel 108 with seals 110, 112 is made simultaneously. In other respects, construction of autoclave 100 is similar to that of the embodiments of FIGS. 1 and 2.

The present invention is susceptible to various modifications which may be introduced by those of skill in the art. For example, connecting rods 22, 24, 26, 28 may comprise more or fewer connecting rods, and may even comprise one connecting rod. If a plurality of connecting rods are provided, fewer than all may be utilized to conduct fluids into and from the working chamber.

In another exemplary modification, the lateral wall may be mobile relative to the base. In this modification, fluids and electrical conductors would pass through the lateral wall. The assembly comprising upper and lower end walls and rods connecting the upper and lower end walls would be removable from the lateral wall.

In still another modification, the working chamber may be relocated to be above the upper end wall. The reservoir may be relocated to the lower end wall, or even to a location within the base. Similarly, the condensate retainer may be relocated to the base.

The lower end wall may be formed integrally with the base.

Obviously, the fluid circuits described above may be modified without substantially affecting function of the invention.

It is to be understood that the present invention is not limited to the embodiments described above, but encompasses any and all embodiments within the scope of the following claims.

I claim:

1. An autoclave comprising;
   a chamber comprising a bottom having a peripheral edge and a top having a geometrically similar peripheral edge;

a working space located between said bottom and said top;

at least one rigid connecting member passing through said working space and solidly fixing said bottom to said top;

a peripheral wall extending completely around and between said bottom peripheral edge and said top peripheral edge;

means for moving said peripheral wall relative to said bottom and said top to an operable position, where said peripheral wall spans said bottom and said top, thereby enclosing and sealing said working space between said bottom and said top, and a retracted position where said working space located between said bottom and said top is exposed to the environment; and means for providing steam to said working space.

2. The autoclave according to claim 1, wherein said at least one rigid connecting member has a longitudinal passage extending therethrough, with an opening connecting said passage and said working space, and an extension portion extending beyond at least one of said top and said bottom.

3. The autoclave according to claim 1, further comprising:

a condensate retainer comprising a lip projecting upwardly from said bottom, for preventing condensate, generated by operation of said autoclave, from escaping when said peripheral wall is moved to said retracted position after operating said autoclave.

4. The autoclave according to claim 1, wherein said means for moving said peripheral wall comprises a powered actuator for moving said peripheral wall between said operable position and said retracted position.

5. The autoclave according to claim 4, said powered actuator having structure for fully disengaging said peripheral wall from said bottom and said top when said peripheral wall is in said retracted position.

6. The autoclave according to claim 1, further comprising a vacuum pump and means for drawing water into said working space responsive to operation of said vacuum pump.

7. The autoclave according to claim 6, further comprising a level sensor disposed within said working space, for determining level of condensate collecting therein.

8. The autoclave according to claim 1, further comprising a heating element disposed within said bottom.

9. The autoclave according to claim 1, wherein said top is smaller than said bottom and said peripheral wall is tapered such that said bottom and said top peripheral edges make simultaneous sealing contact with said peripheral wall when it is moved into said operable position.

10. The autoclave according to claim 1, wherein said top and said bottom are generally circular with said bottom being of greater diameter than said top, and said peripheral wall is generally frustoconical with its greater diameter oriented toward said bottom, said top and said bottom cooperating with said peripheral wall to make simultaneous sealing contact around the entire circular circumference of both said top and said bottom when said peripheral wall is moved into said operable position.

11. An autoclave having:

a working chamber comprising a bottom having a periphery and a top having a periphery, at least one connecting member solidly fixing said bottom to said top, said bottom and said top defining a working space therebetween, and a peripheral wall extending around and closing said working space between each said periphery, wherein said at least one connecting member has a passage extending longitudinally through said connecting member, an opening communicating between said passage and said working space, and extends beyond at least one of said top and said bottom;

means for moving said peripheral wall relative to said bottom and said top to an operable position wherein said peripheral wall spans said bottom and said top, thereby enclosing and sealing a working space between said bottom and said top, and a retracted position wherein said peripheral wall exposes said working space located between said bottom and said top;

means for enabling steam to be provided to said working space;

a base for supporting said top, said bottom, and said peripheral wall on a horizontal surface;

a condensate retainer comprising a lip projecting upwardly from one of said bottom and said base, for constraining condensate generated by operation of said autoclave against escaping when said peripheral wall is moved to said retracted position after operating said autoclave;

a powered actuator for moving said peripheral wall between said operable position and said retracted position, said powered actuator having structure for fully disengaging said peripheral wall from said bottom and said top when said peripheral wall is in said retracted position;

a vacuum pump and means for drawing water into said working space responsive to operation of said vacuum pump;

a level sensor disposed within said working space, for determining level of condensate collecting therein; and a heating element disposed within said bottom.

12. The autoclave according to claim 11, said top being smaller than said bottom and said peripheral wall being frustoconical, said top and said bottom cooperating with said peripheral wall to make simultaneous contact with said peripheral wall when said peripheral wall is moved into said operable position.

* * * * *